United States Patent [19]

Fujimura et al.

[11] Patent Number: 5,475,028
[45] Date of Patent: Dec. 12, 1995

[54] 2-AMINOETHANESULFONIC ACID ZINC COMPLEX

[75] Inventors: Hajime Fujimura, Kyoto; Takahiro Yabuuchi, Takarazuka; Teruo Tanaka, Kyoto; Yoichi Nagamura, Toyoake, all of Japan

[73] Assignee: Zaidan Hojin Seisan Kaihatsu Kagaku Kenkyusho, Kyoto, Japan

[21] Appl. No.: 256,446

[22] PCT Filed: Jan. 13, 1993

[86] PCT No.: PCT/JP93/00057

§ 371 Date: Jul. 13, 1994

§ 102(e) Date: Jul. 13, 1994

[87] PCT Pub. No.: WO93/14095

PCT Pub. Date: Jul. 22, 1993

[30] Foreign Application Priority Data

Jan. 14, 1992 [JP] Japan .................................. 4-024642

[51] Int. Cl.$^6$ .......................... A61K 31/315; C07F 3/06
[52] U.S. Cl. .......................... 514/494; 514/894; 514/925; 556/119; 556/130
[58] Field of Search .................................. 556/119, 130; 514/494, 894, 925

[56] References Cited

FOREIGN PATENT DOCUMENTS 6049077  2/1994  Japan .

3025558  12/1993  WIPO .

OTHER PUBLICATIONS

*Chemical Abstracts*, vol. 74, No. 14, Abstract No. 71065p (1971).

International Search Report (1993).

*Primary Examiner*—Porfirio Nazario-Gonzales
*Attorney, Agent, or Firm*—Merchant, Gould, Smith, Edell, Welter & Schmidt

[57] ABSTRACT

The present invention relates to a 2-aminoethanesulfonic acid zinc complex represented by the following formula:

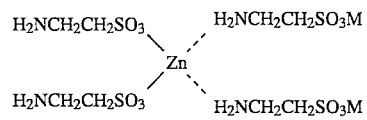

(wherein M is an alkali metal atom), to a process for producing the said complex from 2-aminoethanesulfonic acid and to use of the said complex as an anti-hepatitis agent, liver function improving agent and anti-ulcer agent. The said complex exhibits not only improved physiological activities such as anti-hepatitis activity, suppressory activity against liver-function disorder and anti-ulcer activity but also protective and restorative activity for the digestive tract.

11 Claims, No Drawings

2-AMINOETHANESULFONIC ACID ZINC COMPLEX

This application is a request for U.S. examination under 35 U.S.C. 371 of International application No. PCT/JP93/ 0057, filed on Jan. 13, 1993.

1. Technical Field

The present invention relates to a novel 2-aminoethanesulfonic acid zinc complex, to a process for producing the same and to an anti-hepatitis agent, liver function improving agent and anti-ulcer agent, which individually contain the same as an active ingredient.

2. Background Art

2-Aminoethanesulfonic acid (taurine) has already been known to possess liver-function protecting activity, but much cannot be expected of the compound as an excellent anti-hepatitis and liver-function improving agent, because of its weak physiological activity.

The present inventors, with a specific view to the development of excellent pharmaceuticals from 2-aminoethanesulfonic acid, synthesized numerous derivative compounds and tested them for their pharmacological activities. It was found that a novel 2-aminoethanesulfonic acid zinc complex, among them, can be synthesized by reacting 2-aminoethanesulfonic acid with an alkali agent and zinc compound or by reacting an alkali metal salt of 2-aminoethanesulfonic acid with bis(2-aminoethanesulfonic acid) zinc salt, and the subsequent investigation of its therapeutic effects, toxicological properties and the like revealed that the compound possesses marked anti-hepatitis, liver-function improving and anti-ulcer activities. Such findings, followed by further research work, resulted in the completion of the present invention.

DISCLOSURE OF THE INVENTION

The present invention relates to a 2-aminoethanesulfonic acid zinc complex represented by the general formula:

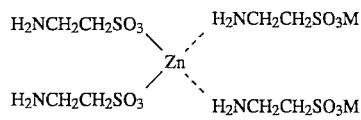

(wherein M is an alkali metal atom), to a process for producing the said complex from 2-aminoethanesulfonic acid and to use of the complex as an anti-hepatitis agent, liver-function improving agent and anti-ulcer agent which individually contain the same as an active ingredient.

As the alkali metal atom represented by M in the general formula (I), there may be mentioned sodium, potassium and the like. The compound of the general formula (I) can be produced, for example, by reacting 2-aminoethanesulfonic acid (1 mole) with an alkali agent (1 mole) and zinc compound (0.25 mole). The reaction, when conducted with use of the zinc compound (0.5 mole), was also found to give the compound of the general formula (I) in the same yield. Referring to the alkali agent, there may preferably be used alkali metal alcoholates such as sodium methylate, sodium ethylate, potassium methylate, potassium ethylate and potassium t-butoxide, while as the zinc compound, zinc acetate is preferred but other zinc compounds may be utilized. The reaction is usually carried out in a suitable solvent such as methanol and ethanol at room temperature or under heating for several minutes to several hours, and after the conclusion of the reaction, the reaction product can be purified by conventional means. Also, the compound of the general formula (I) can be produced by reacting an alkali metal salt of 2-aminoethanesulfonic acid (1 mole) with bis(2-aminoethanesulfonic acid) zinc salt (0.5 mole), wherein as the alkali metal, use is made of sodium, potassium, etc. The reaction is normally conducted in a suitable solvent such as methanol and ethanol at room temperature or under heating for several minutes to several hours and after the reaction is completed, the reaction product can be purified by conventional means.

The compound of the general formula (I) according to the present invention exhibits improved anti-hepatitis, liver-function improving and anti-ulcer activities, while it shows reduced toxicity. The compound can be administered orally or parenterally either per se or after being admixed with pharmacologically acceptable excipients, carriers, diluents, etc. to process into various dosage forms such as tablets, capsules, granules, powders and syrups. The dosage amount varies with the symptoms, age and body weight of patients, route of administration, and the like, and the compound can usually be administered to human adults orally at a single dose of 100 to 200 mg, twice to three times a day.

Described below are examples and test examples of this invention to illustrate the present invention in detail.

EXAMPLES

Example 1

To 12.5 g (0.1 mole) of 2-aminoethanesulfonic acid was added 120 ml of dried methanol, and a solution of 19.3 ml (0.1 mole) of 28% sodium methylate in 50 ml of dried methanol was added dropwise to the resulting solution under stirring at 60° to 70° C., followed by stirring continued under the same conditions. Two hours later, a solution of 5.5 g (0.025 mole) of zinc acetate dihydrate in 60 ml of dried methanol was added dropwise to the solution mixture, and the reaction solution was allowed to cool and stirred for 1 hour. The crystals which precipitated were recovered by filtration and washed with dried methanol to give 14.2 g (yield of 93.4%) of zinc-[bis(2-aminoethanesulfonic acid) bis(sodium 2-aminoethanesulfonate)] in the form of colorless crystals. m.p. 284° C. (decomp.).

Elemental analysis (%): $C_8H_{24}N_4S_4O_{12}Na_2Zn$ Calcd., C:15.80, H:3.98, N:9.22, Na:7.56, Zn:10.76 Found, C:15.87, H:3.97, N:9.21, Na:7.19, Zn:11.20 IR (KBr, cm$^{-1}$); 3449, 3304, 3260, 2988, 2944, 1587, 1456, 1408, 1384, 1209, 1152, 1126, 1044, 984.

Example 2

To 12.5 g (0.1 mole) of 2-aminoethanesulfonic acid was added 120 ml of dried methanol, and a solution of 23.4 ml (0.1 mole) of 30% potassium methylate in 50 ml of dried methanol was added dropwise to the solution under stirring at 60° to 70° C., followed by stirring continued under the same conditions. Two hours later, a solution of 5.5 g (0.025 mole) of zinc acetate dihydrate in 60 ml of dried methanol was added dropwise to the solution mixture, and the reaction mixture was allowed to cool and stirred for another 1 hour. The crystals which precipitated were recovered by filtration and washed with dried methanol to give 14.7 g (yield of 91.9%) of zinc-[bis(2-aminoethanesulfonic acid) bis(potassium 2-aminoethansulfonate)] in the form of colorless crystals. m.p. 274° C. (decomp.).

Elemental analysis (%): $C_8H_{24}N_4S_4O_{12}K_2Zn$ Calcd., C:15.01, H:3.78, N:8.75, K:12.22, Zn:10.21 Found, C:15.02, H:3.76, N:8.79, K:11.80, Zn:10.60 IR (KBr, cm$^{-1}$);

3447, 3295, 3261, 2976, 2937, 1591, 1459, 1405, 1388, 1208, 1152, 1128, 1043, 985.

Example 3

To 12.5 g (0.1 mole) of 2-aminoethanesulfonic acid were added 150 ml of dried methanol and 19.3 ml (0.1 mole) of 28% sodium methylate, followed by stirring for 30 min. Then, 15.7 g (0.05 mole) of bis(2-aminoethanesulfonic acid) zinc salt was added to the solution, followed by stirring at 50° to 60° C. for 5 hours. The precipitate was recovered by filtration and washed with dried methanol to give 27.5 g (yield of 90.5 %) of zinc-[bis(2-aminoethanesulfonic acid-).bis(sodium 2-aminoethanesulfonate)] in the form of colorless crystals. m.p., 284° C. (decomp.).

Elemental analysis (%): $C_8H_{24}N_4S_4O_{12}Na_2Zn$ Calcd., C:15.80, H:3.98, N:9.22, Na:7.56, Zn:10.76 Found, C:15.73, H:4.00, N:9.23, Na:7.31, Zn:11.28 IR (KBr, $cm^{-1}$); 3446, 3303, 3260, 2985, 2944, 1588, 1456, 1408, 1384, 1209, 1152, 1126, 1044, 984.

Test Example

Test substance: Zinc-[bis(2-aminoethanesulfonic acid-).bis(sodium 2-aminoethanesulfonate)] (hereinafter referred to briefly as "FTZ")

1. Anti-hepatitis test (1) Liver disorder (hepatopathy) in mice

A group of 8 dyy-strain male mice (weighing 23 to 25 g), kept fasting from the previous day was treated by intraperitoneal injection of a 25% solution of carbon tetrachloride in olive oil at a dose of 0.1 ml/g body weight and thereafter allowed free access to food. Three hours after the administration of carbon tetrachloride, the mice were given a 1.0 mg/ml concentrated suspension of the test substance, as prepared in conjunction with powdered gum arabic, by intra-peritoneal injection at a dose of 0.1 ml/body weight. Twenty four hours after the administration of carbon tetrachloride, blood samples were drawn from the mice under anesthesia with ether through the abdominal descending aorta. The collected blood was centrifuged at a rate of 3,000 rpm for 15 min, followed by measurement of the activities of alanine transaminase (ALT), aspartate transaminase (AST) and lactate dehydrogenase (LDH) by means of the Lippie method.

The results are shown in Table 1.

cells/mi. Into 2 ml of the suspension in an Erlenmeyer flask of a 10 ml capacity was put a test tube of about 0.5 capacity containing carbon tetrachloride to saturate the reaction system with carbon tetrachloride vapor, and after the flask was tightly stoppered, preincubation was carried out at 37° C. for 5 min. One ml of a test substance solution prepared at a concentration of 0.1 mg/ml Hunk's solution was added to the suspension of liver cells, while 1 ml of Hunk's solution was added to the control. A specifically determined volume of the reaction solution was pipetted out 0 and 10 min after the initiation of reaction, respectively, and immediately centrifuged under 500 g for 30 seconds, and the ALT and AST as leached out into the supernatant liquid were determined for activity by the Lippie method. The results are shown in Table 2.

TABLE 2

| Test substance | ALT IU, mean ± S.D. | AST IU, mean ± S.D. |
|---|---|---|
| Normal group | 78.7 ± 10.6 | 67.8 ± 13.9 |
| Treated group | 1573.7 ± 212.3 | 1356.9 ± 278.2 |
| FTZ | 1107.1 ± 168.8* | 345.7 ± 72.8* |
| Thiopronine | 1426.9 ± 199.5 | 956.8 ± 219.5* |
| Glutathione | 1176.1 ± 123.7* | 321.7 ± 94.4* |
| Glycyrrhizin | 1089.7 ± 210.2 | 267.8 ± 78.1* |

Note:
n = 8.
*Level of significance $p < 0.05$ b. Antibody against rat liver cell membranes Isolated liver cells of rats were prepared by means of Segren's collagenase irrigation method, whereby a liver cell suspension was prepared at a concentration of $6 \times 10^8$ liver cells/mi. An Erlenmeyer flask of a 10 ml capacity in which 2 ml of the suspension had been placed was saturated with 95% oxygen, and after the flask was tightly stoppered, preincubation was carried out at 37° C. for 5 min. One ml of a test substance solution prepared at a concentration of 0.1 mg/ml Hunk's solution was added to the liver cell suspension, while 1 ml of the Hunk's solution was added to the control, followed by incubation for another 5 min, and antiserum against rat liver cell membranes (a 50-fold diluted serum) was added. A specifically determined volume of the reaction solution was pipetted out 0 and 30 min after the initiation of reaction, respectively, and immediately centri-

TABLE 1

| Test substance | ALT IU, mean ± S.D. | AST IU, mean ± S.D. | LDH IU, mean ± S.D. |
|---|---|---|---|
| Normal group | 107.1 ± 54.7 | 86.6 ± 29.2 | 884 ± 335.2 |
| Treated group | 11408 ± 4240.1 | 10663 ± 2493.2 | 44280 ± 9637 |
| FTZ | 4265.7 ± 1347.6* | 3215.8 ± 967.7* | 15865 ± 5300.8* |
| Thiopronine | 4941.2 ± 1537.7* | 4884.5 ± 1097.5* | 26789 ± 9753* |
| Glutathione | 19423.1 ± 1042.3* | 9643.6 ± 3874.3 | 32392 ± 7906* |
| Glycyrrhizin | 8339.3 ± 2420.1 | 8949.6 ± 4530.0 | 26457 ± 11086* |

Note:
*Level of significance $p < 0.05$ (2) Disorder of the isolated liver cells a. Carbon tetrachloride Isolated liver cells of rats were prepared by means of Segren's collagenase irrigation method, whereby a liver cell suspension was prepared to a concentration of $6 \times 10^8$ liver fuged under 500 g for 30 seconds, and the ALT, AST and LDH as leached out into the supernatant liquid were determined for activity by the Lippie method. The results are shown in Table 3.

TABLE 3

| Test substance | ALT IU, mean ± S.D. | AST IU, mean ± S.D. | LDH IU, mean ± S.D. |
|---|---|---|---|
| Normal group | 135.2 ± 23.4 | 94.7 ± 25.6 | 228.7 ± 63.2 |
| Treated group | 2562.4 ± 763.8 | 1826.2 ± 562.4 | 3459.8 ± 578.5 |
| FTZ | 1429.5 ± 327.8* | 1025.8 ± 268.4* | 1875.3 ± 437.1* |
| Thiopronine | 1826.5 ± 479.5 | 1623.7 ± 432.8 | 2583.7 ± 634.1* |
| Glutathione | 2257.8 ± 581.6* | 1759.4 ± 394.3 | 2541.1 ± 563.4* |
| Glycyrrhizin | 1764.8 ± 437.1* | 1358.4 ± 324.1 | 2163.1 ± 562.7* |

Note:
n = 8.
*Level of significance p < 0.05

As is evident from Tables 1 to 3, FTZ of this invention exhibited significantly enhanced suppression against increases in activities of ALT, AST and LDH, as compared with the control compounds that have currently been in use as a therapeutic agent.

2. Anti-ulcer test

Used in the test as an experiment animal were 6-week old, male rats of KBL Wistar strain that had been observed to produce no abnormalities in general conditions after being subjected to acclimatization for about one week from their purchase.

(1) Stomach injury with hydrochloric acid/ethanol:

Rats weighing 193 to 228 g were fasted with free access to water for 24 hours before being used in the experiment. The rats were divided into groups each consisting of 10 heads in such a way as their mean body weights were nearly uniform, treated through oral administration of hydrochloric acid/ethanol (0.15 mole hydrochloric acid solution in 80% ethanol) at a dose of 5 ml/kg body weight and sacrificed through cervical vertebrae dislocation 1 hour after administration. The stomachs were removed and treated with formalin, and individual ulcers formed in the glandula portion of the stomach were measured in length (mm), with the measured ulcer lengths being summed for each rat. The test substance was suspended in a 0.5% aqueous solution of sodium carboxymethylcellulose, and the suspension was given to the test group orally at a dose of 10 ml/kg body weight 30 min before administration of hydrochloric acid/ethanol, whereas the vehicle alone was applied to the control group. The results are shown in Table 4.

TABLE 4

| Test substance | Dose (mg/kg) | Suppression rate (%) | $UD_{50}$ (mg/kg) (95% C.L.) |
|---|---|---|---|
| Control group | — | — | |
| FTZ | 50 | 32.1 | 88.7 |
| | 100 | 53.5* | (83.4–94.3) |
| | 200 | 74.9* | |

Note:
*Level of significance, p < 0.01.

(2) Stomach injury through water-immersion constraint stress

Rats weighing 183 to 235 g were fasted with free access to water for 24 hours before being used in the experiment. The rats were divided into groups each consisting of 10 heads in such a way as their mean body weights were nearly uniform, stress-loaded by soaking the animals as placed in a stress cage of Univ. of Tokyo type in a water tank at 23° C. up to the xiphoid and sacrificed through cervical vertebrae dislocation 7 hours later. The stomachs were removed and treated with formalin, and individual ulcers formed in the glandula portion of the stomach were measured in length (mm), with the measured ulcer lengths being summed for each rat. The test substance was suspended in a 0.5% aqueous solution of sodium carboxymethylcellulose, and the suspension was given to the test group orally at a dose of 10 ml/kg body weight 30 min before the water-soaking constraint, whereas the vehicle alone was applied to the control group. The results are shown in Table 5.

TABLE 5

| Test substance | Dose (mg/kg) | Suppression rate (%) | $UD_{50}$ (mg/kg) (95% C.L.) |
|---|---|---|---|
| Control group | — | — | |
| FTZ | 50 | 26.4* | 105 |
| | 100 | 56.1* | (97.9–113) |
| | 200 | 64.5* | |

Note:
*Level of significance p < 0.05.

The above results suggest that the compound of this invention exhibits anti-hepatitis, liver-function improving and anti-ulcer activities, whereas 2-aminoethanesulfonic acid (taurine) was found to produce much lower corresponding effects.

3. Acute toxicity test

Male, SLC:ICR (SPE) mice weighing 20 g, divided into groups each consisting of 5 heads, were treated by oral administration of the test compound suspended in gum arabic at doses of 1,000 mg/kg, 1,500 mg/kg and 2,500 mg/kg test compound, followed by observation for any abnormalities. As a result, the compound of this invention at doses up to 2,500 mg/kg $LD_{50}$ value did not cause any animal to die.

Consequently, the compound of this invention was confirmed to show markedly enhanced degree of safety in comparison with its effective amount.

Industrial Applicability

Taurine, which exhibits very weak liver-function protecting activity but is nearly free from toxicity, can form a complex with zinc to thereby give the compound of this invention that greatly facilitates the intake of zinc into liver cells as compared with conventional inorganic zinc salts and develops through synergism both better liver-disorder preventive activity than the existing anti-hepatitis agents. Furthermore, the finding that the compound shows a distinct mucosa-protective and restorative effect for the digestive tract, coupled with its remarkably enhanced degree of safety, indicates clinically significant utility for the compound.

We claim:

1. A 2-aminoethanesulfonic acid zinc complex represented by the general formula:

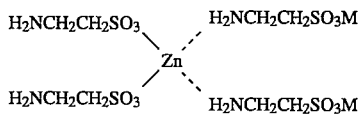

(wherein M is an alkali metal atom).

2. A zinc complex according to claim 1, wherein M is sodium or potassium.

3. A process for producing a 2-aminoethanesulfonic acid zinc complex represented by the general formula:

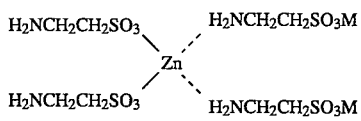

(wherein M is an alkali metal atom), characterized in that said process comprises reacting 2-aminoethanesulfonic acid with an alkali agent and a zinc acetate.

4. A process according to claim 3, wherein the alkali agent is an alkali metal alcoholate.

5. A process for producing a 2-aminoethanesulfonic acid zinc complex represented by the general formula:

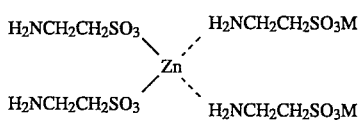

(wherein M is an alkali metal atom), characterized in that said process comprises reacting an alkali metal salt of 2-aminoethanesulfonic acid with bis(2-aminoethanesulfonic acid)zinc salt.

6. An anti-hepatitis composition, which comprises an amount effective in treating hepatitis of a 2-aminoethanesulfonic acid zinc complex as claimed in claim 1 and a pharmaceutically acceptable carrier.

7. A liver function improving composition, which comprises a 2-aminoethanesulfonic acid zinc complex as claimed in claim 1 in an amount effective for improving liver function, and a pharmaceutically acceptable carrier.

8. An anti-ulcer composition, which comprises a 2-aminoethanesulfonic acid zinc complex as claimed in claim 1 in an amount effective in treating ulcers, and a pharmaceutically acceptable carrier.

9. A method of treating hepatitis, comprising administering to a human subject in need thereof an effective amount of a 2-aminoethanesulfonic acid zinc complex as claimed in claim 1.

10. A method of improving liver function comprising administering to a human subject in need thereof an effective amount of a 2-aminoethanesulfonic acid zinc complex as claimed in claim 1.

11. A method of treating ulcers comprising administering to a human subject in need thereof an effective amount of a 2-aminoethanesulfonic acid zinc complex as claimed in claim 1.

* * * * *